(12) United States Patent
Lee et al.

(10) Patent No.: US 9,597,136 B2
(45) Date of Patent: Mar. 21, 2017

(54) APPARATUS FOR REINFORCING BONE AND TOOLS FOR MOUNTING THE SAME

(71) Applicant: CHANG GUNG UNIVERSITY, Taoyuan County (TW)

(72) Inventors: Shiuann-Sheng Lee, Taipei (TW); Wen-Jer Chen, Taipei (TW); Ching-Lung Tai, Taoyuan County (TW); De-Mei Lee, Taipei (TW); Jiunn-Jong Wu, Taipei (TW); Chih-Ta Yu, New Taipei (TW); Tsung-Hsin Wu, Taipiei (TW); Sheng-Yu Lin, Kaohsiung (TW)

(73) Assignee: CHANG GUNG UNIVERSITY, Taoyuan County (TW)

( * ) Notice: Subject to any disclaimer, the term of this patent is extended or adjusted under 35 U.S.C. 154(b) by 83 days.

(21) Appl. No.: 13/938,368

(22) Filed: Jul. 10, 2013

(65) Prior Publication Data
US 2014/0135780 A1    May 15, 2014

Related U.S. Application Data

(60) Provisional application No. 61/761,696, filed on Feb. 7, 2013.

(30) Foreign Application Priority Data

Nov. 13, 2012   (TW) .............................. 101142160 A (51) Int. Cl.
*A61B 17/88* (2006.01)
*A61F 2/44* (2006.01)
(Continued)

(52) U.S. Cl.
CPC ...... *A61B 17/8811* (2013.01); *A61B 17/7098* (2013.01); *A61B 17/8819* (2013.01);
(Continued)

(58) Field of Classification Search
CPC . A61B 17/7097; A61B 17/7098; A61B 17/84; A61B 17/844;
(Continued)

(56) References Cited

U.S. PATENT DOCUMENTS

4,453,539 A * 6/1984 Raftopoulos ...... A61B 17/7258
606/63
5,059,193 A * 10/1991 Kuslich .......................... 606/247
(Continued)

*Primary Examiner* — Matthew Lawson
*Assistant Examiner* — Amy Sipp (57) ABSTRACT

An apparatus, for reinforcing bone and tools for mounting the same, has an implant including a barrel and a device. The implant can be expanded by an expanding apparatus including an outer tub, a base, a hollow body and a handle. The expanding apparatus can be bound to the implant to place the implant into a bone to be treated and adjust the expansion degree. The expanding apparatus can be replaced by an injector apparatus including a container for bone cement and an injecting handle. The injector apparatus can inject a mixture for reinforcing bone (e.g., bone cement) into the bone through an exit, the device, the aperture, the barrel and the window of the barrel, and into the to-be treated area.

10 Claims, 13 Drawing Sheets

(51) Int. Cl.
*A61B 17/70* (2006.01)
*A61F 2/46* (2006.01)

(52) U.S. Cl.
CPC ...... *A61B 17/8825* (2013.01); *A61B 17/8858* (2013.01); *A61F 2/44* (2013.01); *A61F 2/4601* (2013.01); *A61F 2/4611* (2013.01); *A61F 2002/4602* (2013.01)

(58) Field of Classification Search
CPC ............ A61B 17/8802–17/8827; A61B 17/885–17/8858; F16B 13/04–13/063; F16B 13/0841
See application file for complete search history.

(56) References Cited

U.S. PATENT DOCUMENTS

| | | | | |
|---|---|---|---|---|
| 6,592,589 | B2* | 7/2003 | Hajianpour | 606/95 |
| 2009/0005782 | A1* | 1/2009 | Chirico | A61B 17/1617 606/63 |
| 2011/0029082 | A1* | 2/2011 | Hall | A61B 17/68 623/17.11 |
| 2013/0226251 | A1* | 8/2013 | Chegini | A61B 17/844 606/325 |

* cited by examiner

APPARATUS FOR REINFORCING BONE AND TOOLS FOR MOUNTING THE SAME

FIELD OF INVENTION

The embodiments disclosed herein relate to bone strengthening and reinforcing and, more particularly, to internal bone fixation devices and methods of using such devices for repairing a weakened or fractured bone.

BACKGROUND

Bone is a living tissue and plays a structural role in the body. Unfortunately, over millions of patients in the world are diagnosed with bone damage because of various reasons. Bone defects caused by osteonecrosis, bone tumor resection, or osteoporotic fracture are often treated by a bone grafting procedure. Whether utilizing autogenic, allogenic, or synthetic grafts, the processes of creeping substitution and remodeling are essential for the healing of the bone defects. It is, however, mechanically undesirable during the remodeling stage, because the grafts will lose their supporting strength gradually. Without adequate mechanical support, the bone defects might collapse or deform and could not sustain the physical loading in daily activities. Fracture repair is required to restore a damaged or weakened bone structure in order to endure the applied strength or stress to a body. Several different treatment methods have been developed in the past few decades in order to facilitate or expedite the recovery process. More particularly, a surgical approach adopted by a lot of physicians is to provide an external treatment. Implantation of bone void fillers, such as bone cement in a fractured bone, is less invasive and is being increasingly applied during surgical procedures. The device or apparatus utilized by an operator during implantation is required to be more user-friendly and feasible. A reinforcement with an empty chamber to be filled by the bone reinforcing mixture such as cement may be inserted into the damaged area. A typical device for bone cement injection has a tube-like shaped body, which delivers a cartridge containing bone cement into the reinforcement. Usually the reinforcement is left in the body to support bone strength. Ideally, the stiffness of the reinforcement must be enough to resist stress in order to maintain a desired shape either during the surgery or being left out from the body after treatment. Unfortunately, to prevent undesired deformation of the implanted reinforcement is still a major challenge.

SUMMARY OF THE INVENTION

Devices and methods for reinforcing a weakened or damaged bone are disclosed herein. According to one aspect illustrated herein, provided is a device including a rigid tube encased by a barrel that can be expanded to a desired shape by an externally applied force through a gear. The tube has a tapered end distal to the cap, an aperture proximal to the cap, and a threaded inner wall proximal to the tapered end, which allows the barrel to be desirably positioned on the tube. The barrel has a securing part and an adjustable part. The device has a lumen that can be operated as a cannulated device by minimally invasive methods. The device has multiple apertures for delivering bone reinforcing mixtures to a bone.

According to one aspect illustrated herein, provided is an apparatus for reinforcing a bone including a cap, and a substantially rigid tube adjacent to the cap. The tube has a tapered end distal to the cap, an aperture proximal to the cap, and a threaded inner wall proximal to the tapered end to allow the apparatus to be securely handled. The apparatus further includes a barrel which is designed to encase the tube, and the barrel has a securing portion which is allowed to be moved toward the cap in response to an external force and to be fixed at a desired position proximal to the tapered end of the tube.

According to another aspect illustrated herein, provided is a system for reinforcing a bone including an expandable barrel with a rigid tube which has a tapered end distal to the cap, an aperture proximal to the cap, and a threaded inner wall proximal to the tapered end to allow the apparatus to be securely handled. The apparatus further includes a barrel which is designed to encase the tube, and the barrel has a securing portion which is allowed to be moved toward the cap in response to an external force and to be fixed at a desired position proximal to the tapered end of the tube. The system is operated by a gear with a mechanism to exert an external force to the barrel. One end of the gear is designed to be locked with the threaded inner wall of the tube.

Various embodiments provide certain advantages. Not all embodiments of the circumstances. Further features and advantages of the embodiments are described in detail below with reference to the accompanying drawings.

BRIEF DESCRIPTION OF THE DRAWINGS

The presently disclosed embodiments will be further explained with reference to the attached drawings, wherein like structures are denoted as the accompany drawings. The drawings shown are not necessarily to scale, with emphasis instead generally being placed upon illustrating the principles of the presently disclosed embodiments.

DETAILED DESCRIPTION OF THE INVENTION

The embodiments of the present invention are described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein. Rather, these embodiments are provided so that this disclosure will be thorough and complete, and will fully convey the scope of the invention to those skilled in the art. As used herein, the term "or" is an inclusive "or" operator, and is equivalent to the term "and/or," unless the context clearly dictates otherwise. In addition, throughout the specification, the meaning of "a", "an" and "the" include plural references. The term "coupled" implies that the elements may be directly connected together or may be coupled through one or more intervening elements.

Figure 1A:
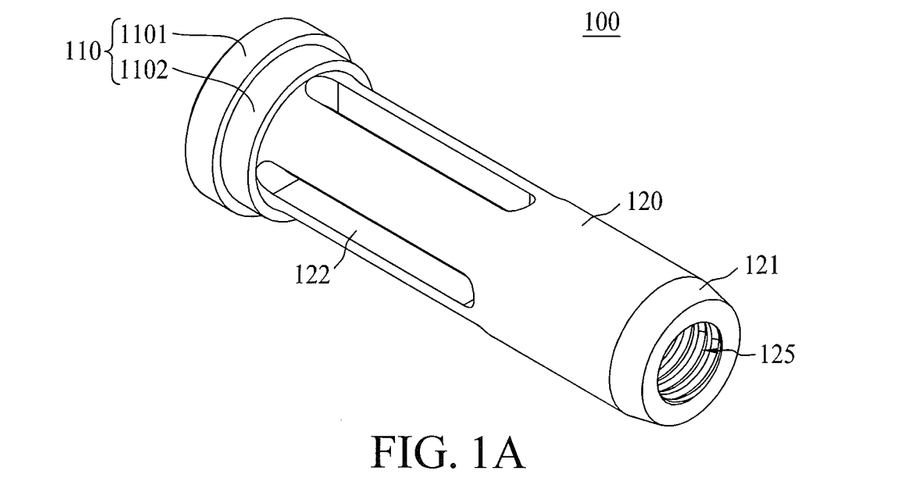
FIGS. 1A-1B show expanded views of a rigid tube component of a device for reinforcing a bone according to an illustrative embodiment of the present invention.
Figure 1B:
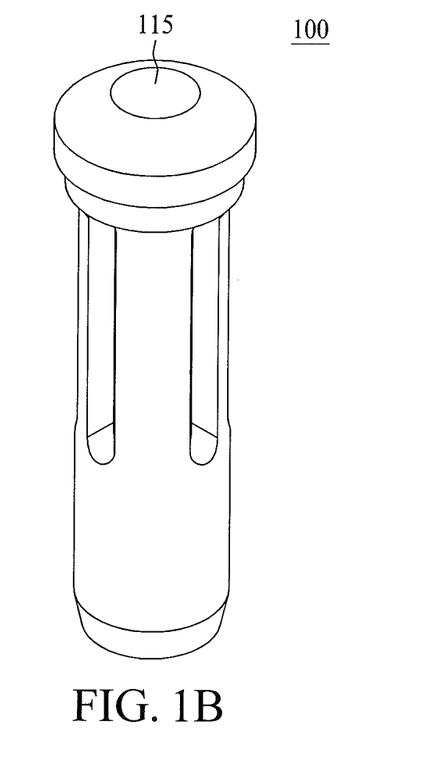

Main components of an embodiment of a device for fixing an apparatus for reinforcing a weakened or fractured bone are shown in FIG. 1A and FIG. 1B. The device 100 includes a cap 110 which is at one end of the device. The device 100 further includes a tube 120 with an elongated shape. The cap 110 is at one end of the tube 120. In an embodiment, the cap 110 and the tube 120 are formed from the same rod or bulk in order to possess a better rigidity or stiffness, and the cap 110 may have a through hole 115 at the center. The cap 110 may be composed of two annuli 1101 and 1102 as shown in FIG. 1A. The annulus 1101 with a larger diameter is disposed farther away from a tapered, tube end 121 of the tube 120 compared to the annulus 1102. The tube 120 is preferably made with a material such as metal or its alloy. In some embodiments, titanium or its alloy may be selected. In other embodiments, the tube 120 can be either constructed from a single metal, such as stainless steel, and gold or from composite materials such as fiber reinforced metal. Preferably, the tube 120 is rigid or substantially rigid in order to resist or minimize deformation under any applied external force. Moreover, the tube 120 further includes a lumen. The lumen may extend through the cap 110 to form a tunnel which opens at both ends of the device 100. In an embodiment, the tapered, tube end 121 distal to the cap 110 is preferably designed as a tapered shape as shown in FIG. 1A. The tapered angle can be between 0 to 45 degrees. Preferably, it can be between 0 to 30 degrees. In some embodiments according to the present disclosure, the angle is designed to be between 2 to 15 degrees. One of the purposes of introducing a tapered end design is to facilitate the tube 120 sliding into a press-fitting outer barrel 200 which may have an inner diameter designed to be interlocked with the outer diameter of the tube 120. The tube 120 can further include at least one aperture 122 which is disposed proximally to the cap 110. The aperture 122 can be formed of various shapes such as a circle, slot, and triangle, and the aperture 122 allows materials to pass into and out of the tube 120. In an embodiment, the inner wall of the tube 120 proximal to the tapered, tube end 121 can be threaded. With a threaded inner wall 125, the device 100 can be easily fastened with a gear (not shown) which is designed to accurately dispose or implant the device 100 at a desired fracture or weakened bone position.

Those skilled in the art should recognize that the term "bone" used herein can be referred to vertebrae, tibia, fibula, humerus, ulna, radius and other bones and still be within the scope and spirit of the disclosed embodiments.

Figure 2:
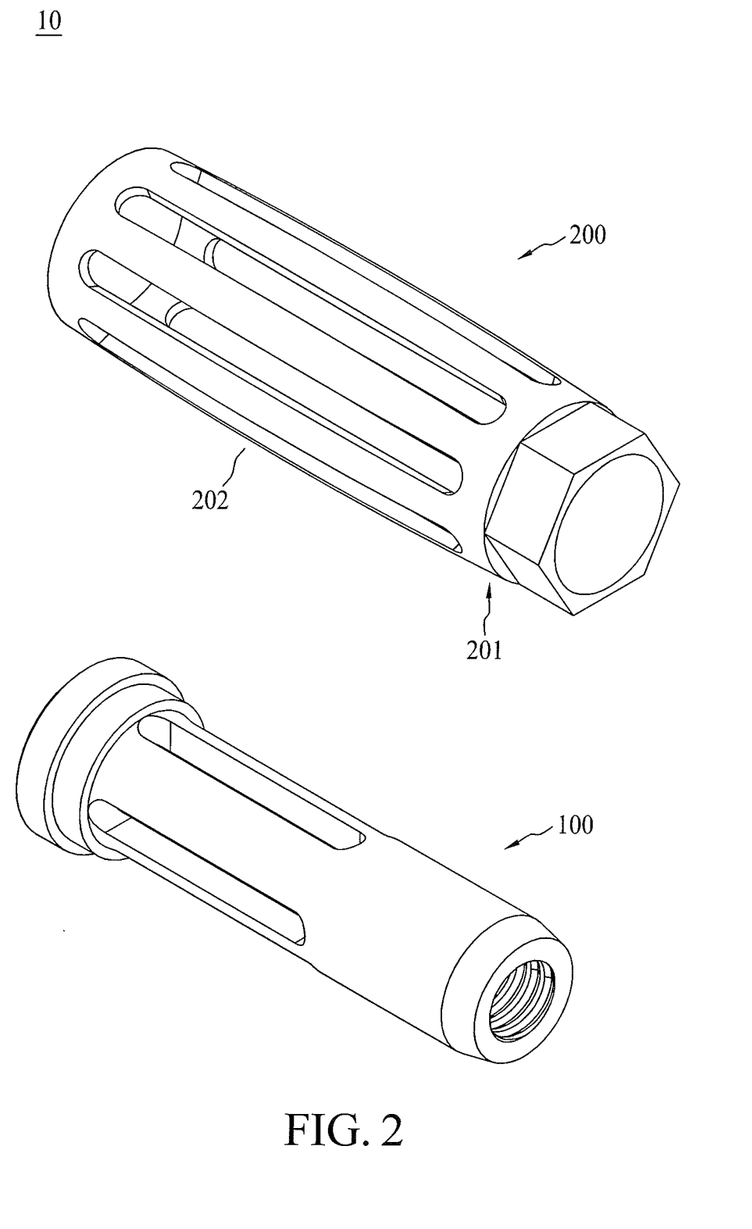
FIG. 2 shows an expanded view of an apparatus including a barrel component and a rigid tube component for reinforcing a bone according to an illustrative embodiment of the present invention.

The present disclosure further discloses an apparatus 10 for reinforcing a weakened or fractured bone as shown in FIG. 2. The apparatus 10 includes a device 100 and a barrel 200. The device 100 can be the same as the aforementioned device 100 or can be slightly modified to fit in the apparatus 10. The elongated barrel 200 includes a securing part 201 at one end. The barrel 200 further includes an adjustable part 202 adjacent to the securing part 201. In an embodiment, the securing part 201 is connected with the adjustable part 202, and the term "connected" used herein may refer to any connecting ways and should not be limited to such as jointed, welded, mounted, integrated, or as an integral unit. In an embodiment, the securing part 201 and the adjustable part 202 are formed/machined from the same piece of rod or bulk in order to possess a better rigidity or stiffness. The materials selected for the barrel 200 can be metal or its alloy. In an embodiment, the material selected for the barrel is the same as that of the device 100. In some embodiments, titanium or its alloy may be selected. In other embodiments, the tube 120 can be constructed of a single metal, such as stainless steel, and gold, or be constructed of a composite material such as fiber reinforced metal. The barrel 200 may have a lumen inside. In other words, both the securing part 201 and the adjustable part 202 are hollow in order to be assembled with the device 100. The inner diameter (if the hollowed-out pattern is circular) of the securing part 201 can be designed to be press fitted with the adjustable part 202. The outer rim of the securing part 201 can be trimmed to different shapes such as circular or polygonal. In an embodiment, the securing part 201 is hexagonal-shaped or a shape of the combination of rectangle and circle. In an embodiment, the securing part 201 is a bolt head with a through hole as shown in FIG. 2.

FIG. 2 depicts a tubular adjustable part 202. Those skilled in the art should recognize that the adjustable part is not limited to a tube or a cannula. In an embodiment, a part of the adjustable part 202 is carved out to form at least one slotted or patterned hole in the wall of the adjustable part 202. In another embodiment, a part of the adjustable part 202. Is carved out to form a meshed pattern. The slotted or patterned hole(s) of the adjustable part 202 allows the tubular adjustable part 202 to deform easily when an external force is applied on the barrel 200 along the axial direction of the tubular barrel 200. The hollowed patterns also allow reinforcing materials to flow into and out of the barrel 200. In an embodiment, the adjustable part 202 can expand from a first geometry to a larger volume second geometry, for example, from a tubular shape to a cage, crown, or lantern-like object.

Figure 3:
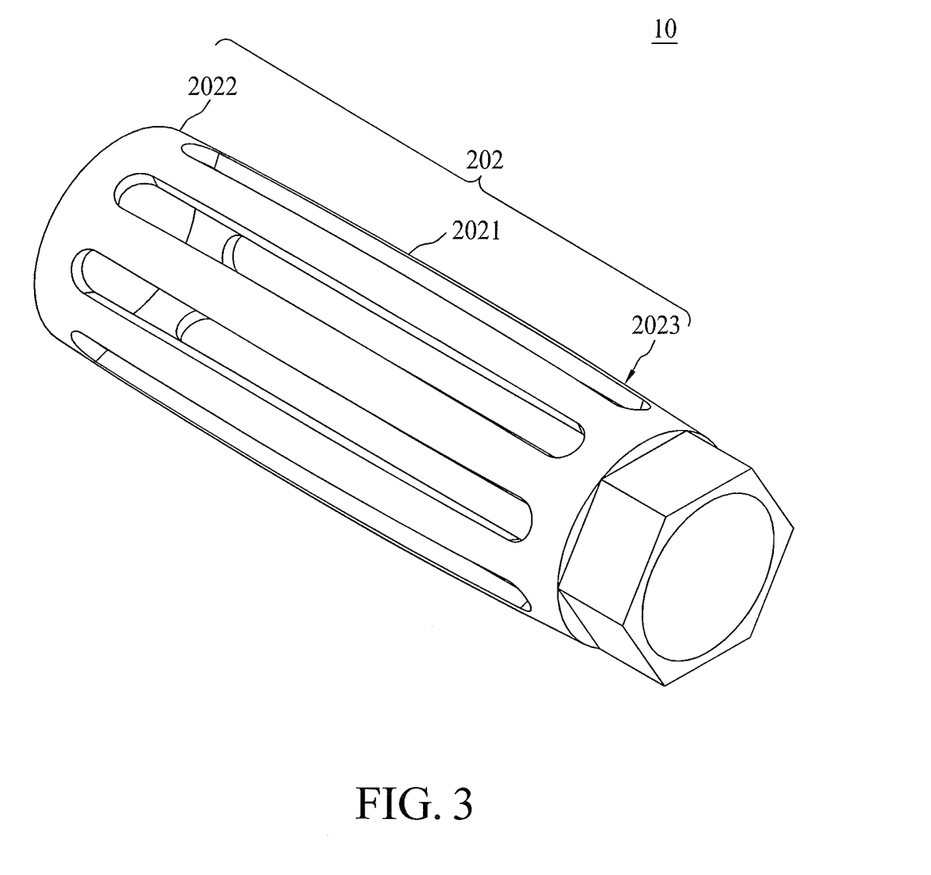
FIG. 3 shows an expanded view of a barrel component of an apparatus for reinforcing a bone according to an illustrative embodiment of the present invention.
Figure 4A:
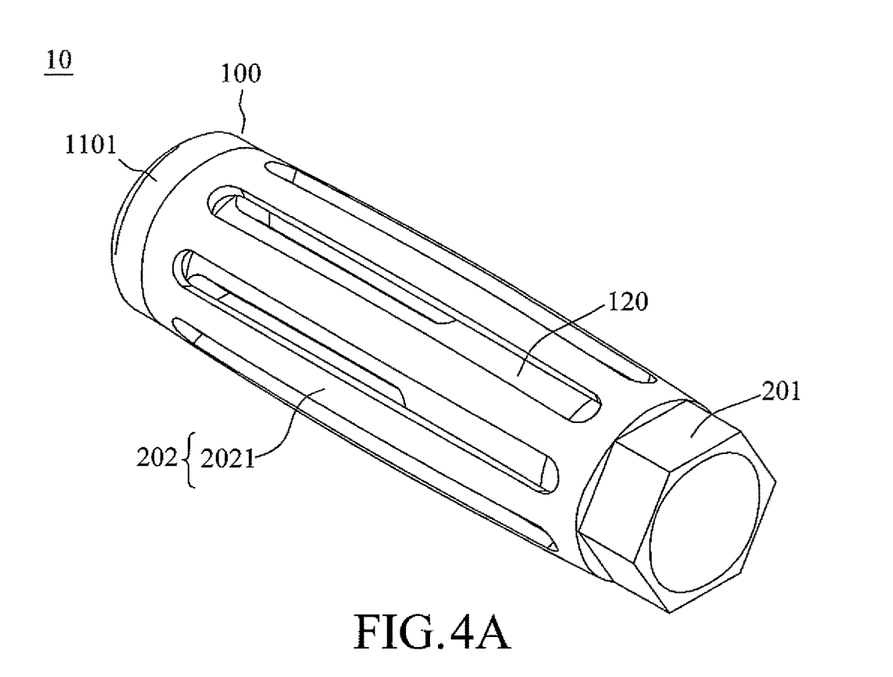
FIG. 4A shows an expanded view of a barrel for reinforcing a bone according to an illustrative embodiment of the present invention.
Figure 4B:
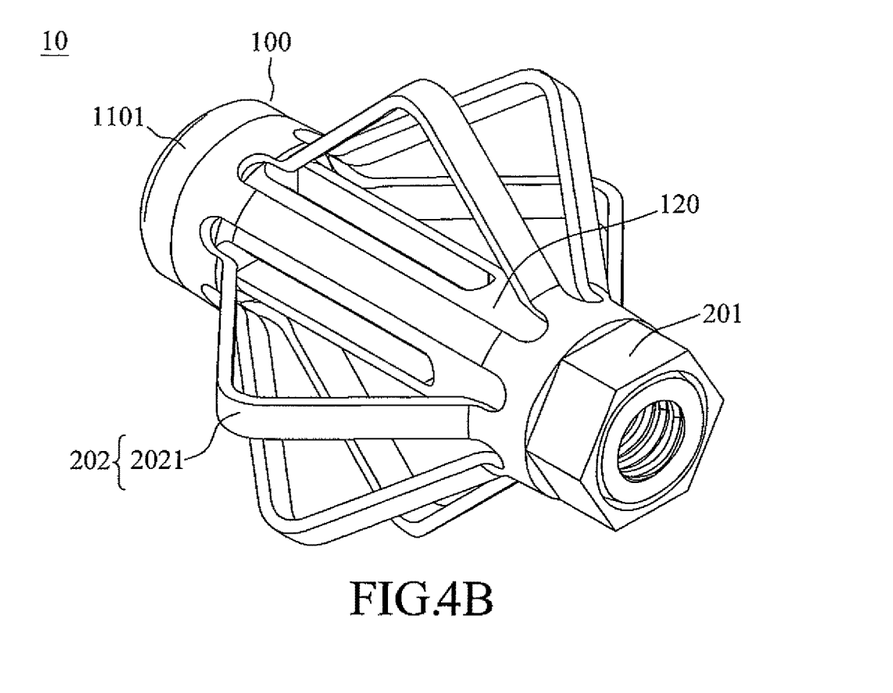
FIG. 4B shows an expanded view of an apparatus for reinforcing a bone being expanded to a desired geometry according to an illustrative embodiment of the present invention.

The outer surface of the adjustable part 202 may be other than straight, and it can be machined to have a curved or bowed outer surface for the purpose of stress distribution. Therefore, the adjustable part 202 may have a straight, convex, or concave outer surface or the combination thereof. In an embodiment, the thickness of the adjustable part 202 is designed to be non-uniform. The thickness variation may help the adjustable part 202 expand to a desired geometry. The barrel 200 of an embodiment as illustrated in FIG. 3 includes an adjustable part 202 with a thickest portion at the intermediate part 2021 which is between two thinner portions 2022 and 2023. The location of the thickest portion may affect the stress distribution when the barrel 200 is under an external force. Therefore, the stress distribution can be modified by changing the expansion geometry of the adjustable part 202. FIG. 4A illustrates an embodiment with an adjustable part 202 with a thickest portion at the center of the intermediate part 2021, allowing the adjustable part 202 to expand to a desired geometry, such as a symmetric or asymmetric cage, as shown in FIG. 4B. In another embodiment, the adjustable part 202 has a thickest portion at the intermediate part 2021 but closer to the securing part 201, allowing the adjustable part 202 to expand to a crown-shaped object. Those skilled in the art should realize that the arrangement of the thickest portion on the adjustable part 202 is not limited to the aforementioned embodiments. Any non-uniform thickness design for the adjustable part is within the scope of the present disclosure, and although the aforementioned embodiments use a slotted pattern for illustration, a meshed design is also included. In another embodiment, the barrel 200 with a mesh-patterned hole adjustable part 202 may expand like a balloon or a lantern.

Figure 5:
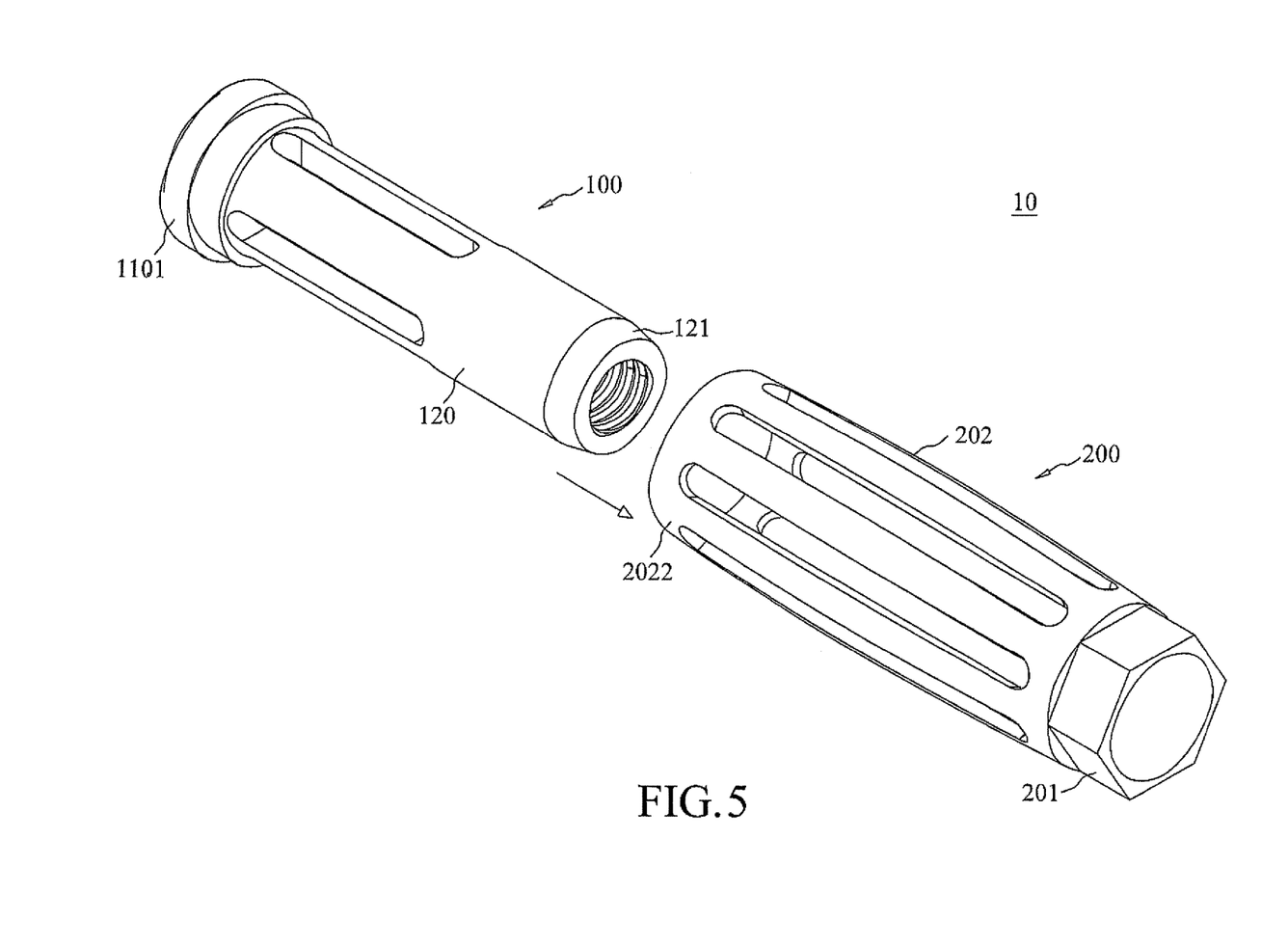
FIG. 5 shows the assembling of two components of an apparatus for reinforcing a bone according to an illustrative embodiment of the present invention.

Referring to FIG. 5, an example of integration of the apparatus 10 is further described. In the apparatus 10, the barrel 200 is designed to encase, enclose or envelope the device 100. In an embodiment, the inner diameter of the securing part 201 is defined to be the same as or substantially the same as the outer diameter of the tube 120. The outer diameter of the annulus 1101 is greater than the inner diameter of the adjustable part 202. The device 100 is inserted or slid into the portion 2022 distal to the securing part 201 with the tapered, tube end 121 inserted first. The device 100 can be placed inside the barrel 200 until the portion 2022 hits the annulus 1101. The tapered, tube end 121 with an outer diameter smaller than the inner diameter of the securing part 201 can move into the securing part 201 with less resistance. Since the inner wall proximal to the tapered, tube end 121 is threaded, a handling gear (not shown here) with a threaded end can be screwed into the apparatus 10 from the securing part 201 of the barrel 200. With the gear engaged, the apparatus 10 can be disposed to any desired location of a fractured or weakened bone during treatment. Those skilled in the art should recognize that the handling gear can be any device or apparatus which is designed for the operator to screw into the apparatus 10, and any variation or modification is within the scope and spirit of the disclosed embodiments.

FIGS. 6-13 illustrate an embodiment of an expanding apparatus 30 according to the present invention and also refer to FIGS. 1-4 for the following description. The expanding apparatus 30 includes an outer tube 400, which has a through hole 402 with a connection portion 403. The connection portion 403 is corresponding to the securing part 201, i.e. the securing part 201 can be inserted and fit into the connection portion 403. At the other end, a base 405 is attached to the outer tube 400 with a hole in connection with the through hole 402. The base 405 further includes a first pressing surface 406.

Figure 6:
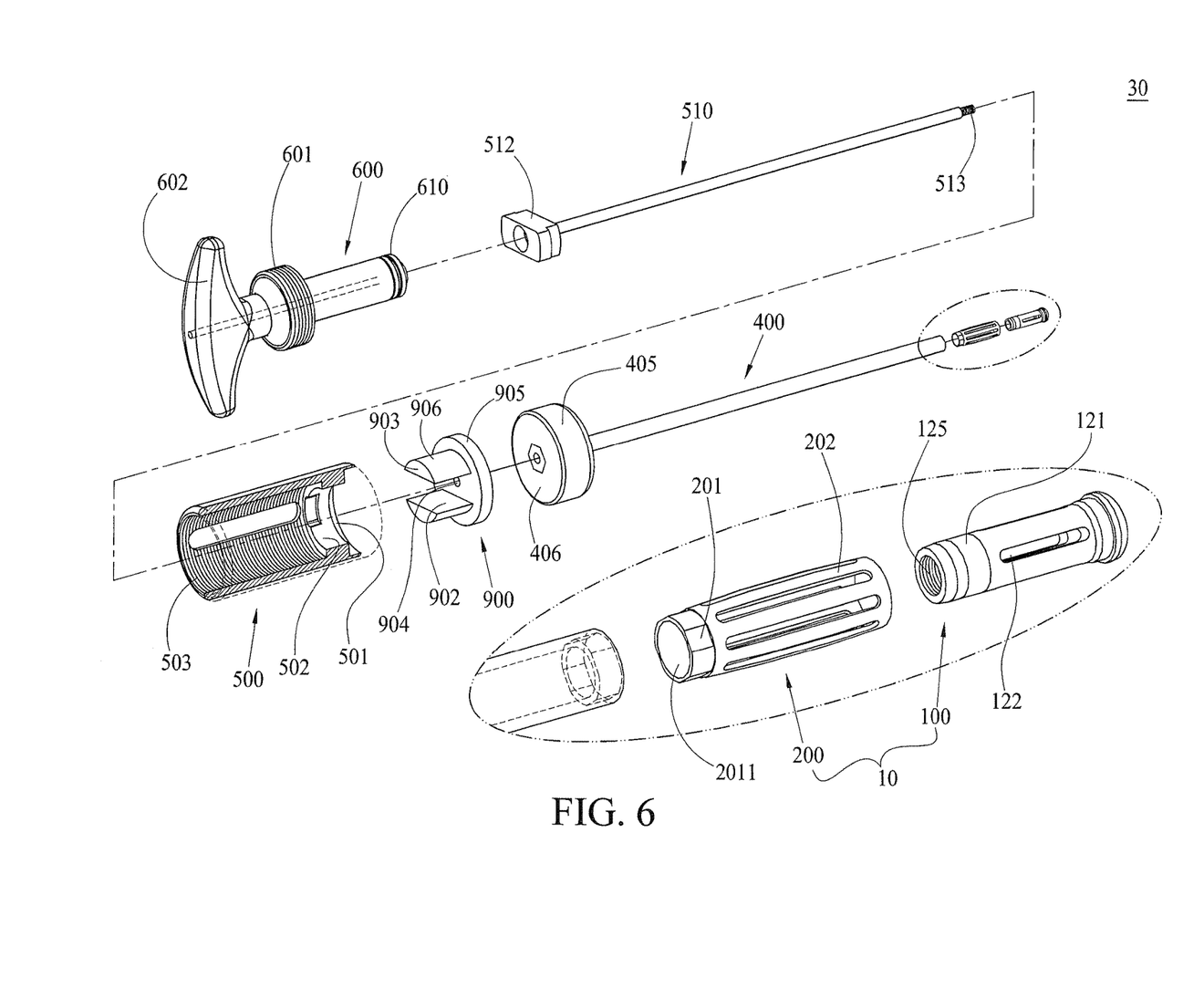
FIG. 6 shows a three-dimensional perspective view of an apparatus for reinforcing a bone (including an expanding apparatus) according to an illustrative embodiment of the present invention.
Figure 7:
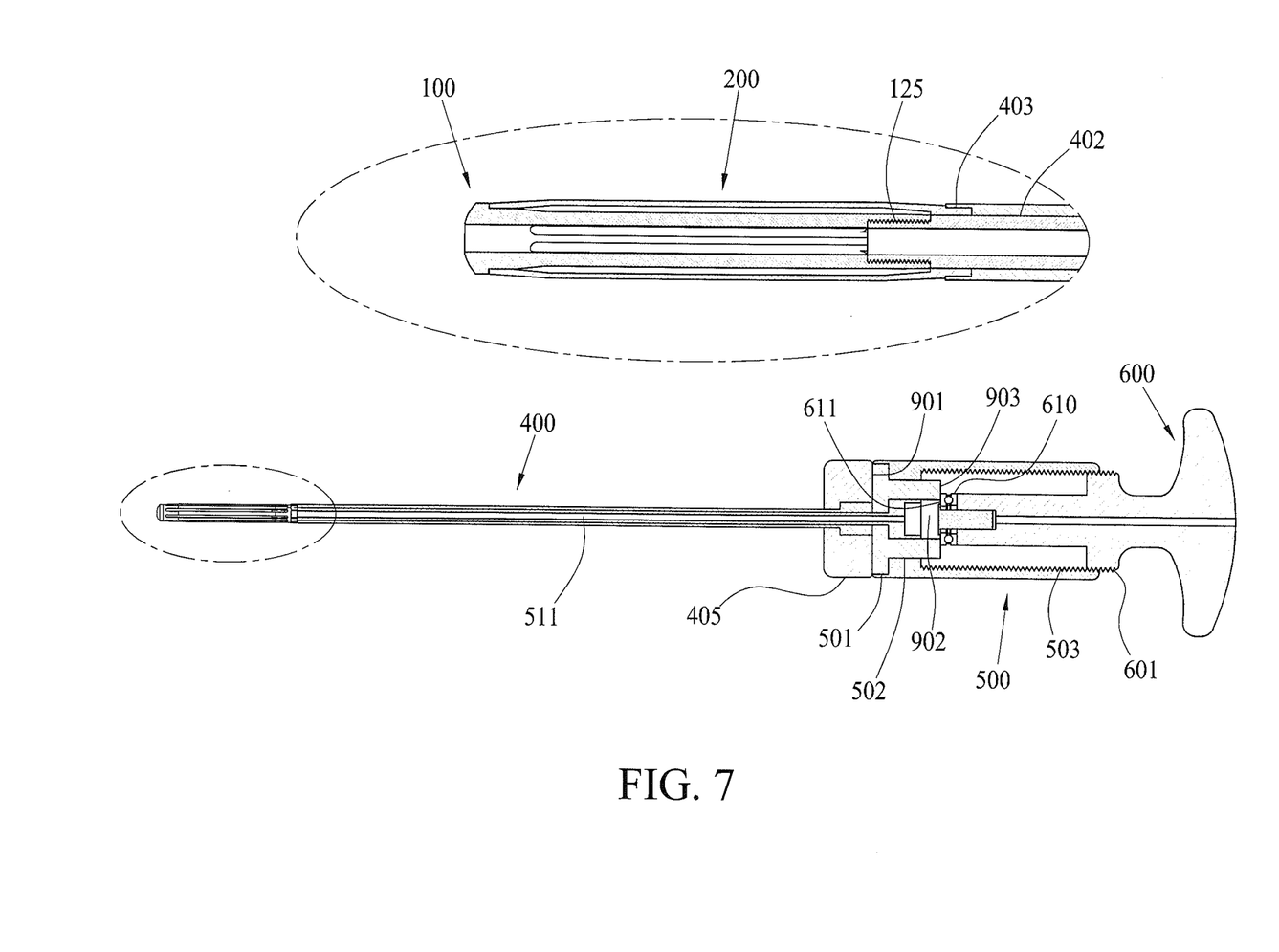
FIG. 7 shows a section view of an apparatus for reinforcing a bone (including an expanding apparatus) according to an illustrative embodiment of the present invention.

As described above, the apparatus of the present invention, as an implant, can be expanded with the expanding apparatus 30, comprising an outer tube 400, an inner coupling member or a packing 900, a hollow body 500, and a handle 600. The outer tube 400 has the through hole 402 axially set within the outer tube 400. The connection portion 403 is set at one end of the outer tube 400 and correspondingly to the securing part 201 with a polygonal shape and chamfered at the edge thereof, and the securing part 201 can be inserted and fit into the connection portion 403. The base 405 is attached to the other side of the outer tube 400 and includes the first pressing surface 406.

One end of the packing 900 forms a second pressing surface 901 against the first pressing surface 406, and a recess 902 is set at the other end of the packing 900. A third pressing surface 903 is formed at the both sides of the recess 902. Further, a first fitting hole 904 (in an axial direction), an outer rim 905 (at the peripheral) and a fitting portion 906 are set on the packing 900.

A second fitting hole 501 and a third fitting hole 502 are sequentially set at one end within the hollow body 500, and a second inner thread 503 is set at the other end. An inner tube 510 is set at the third fitting hole 502, a tunnel 511 is axially set within the inner tube 510, a lock 512 is set at one side of the inner tube 510, and a first external threaded portion 513 is set at the other side of the inner tube 510. The first external threaded portion 513 is linked to the first threaded inner wall 125 of the apparatus (implant) 10, and the inner tube 510 is sequentially fit into the first fitting hole 904 and the through hole 402 to fit the fitting portion 906 into the third fitting hole 502, to fit the outer rim 905 into the second fitting hole 501, and to embed the lock 512 into the recess 902, to restrict the shift of the packing 900 only in the axial direction and not over the outer rim 905 on the hollow body 500.

A second external thread 601 is set outside the handle 600. A steering portion 610, a bearing or a component with similar mechanism, is connected to one side of the handle 600, and a twisting portion 602 is set at the other side of the handle 600 in a wing shape, which is easy for twisting to the user. The second external thread 601 is connected to the second inner thread 503, and the steering portion 610 forms a fourth pressing surface 611.

Figure 10:
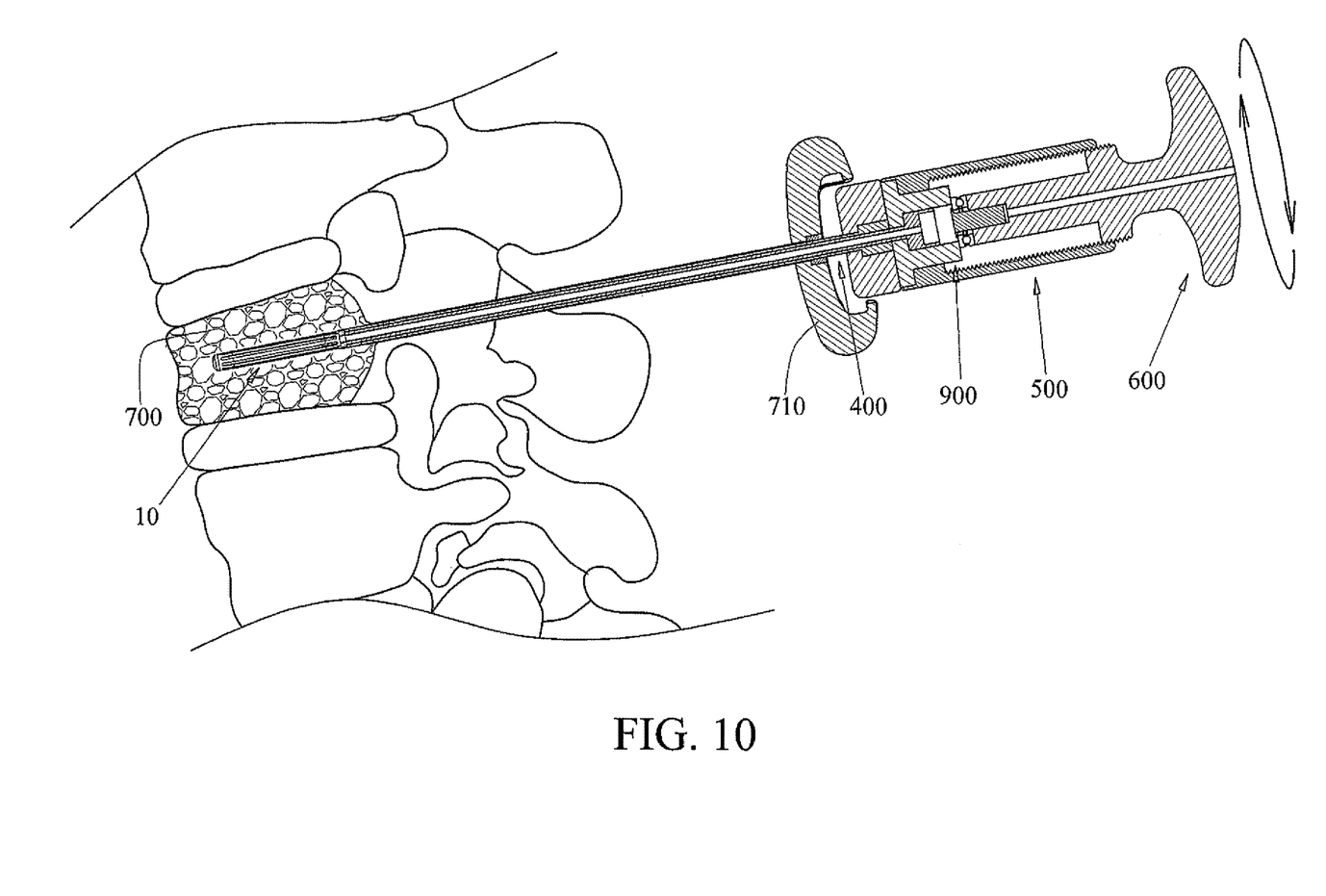
FIG. 10 is a schematic diagram showing the use state of an example of the present invention (implant unexpanded)

The method to use the expanding apparatus 30 can be summarized in the following steps:
a) connecting the connection portion 403 of the outer tube 400 to the securing part 201;
b) rotating the hollow body 500 to thread the first external threaded portion 513 into the threaded inner wall 125;
c) adding an outer tube 710 as shown in FIG. 10 and implanting the apparatus 10 into a part of damaged bone (such as spine) 700;
d) rotating the twisting portion 602 of the handle 600 while holding the hollow body 500, making the fourth pressing surface 611 of the steering portion 610 press the third pressing surface 903 of the packing 900, and also enabling the second pressing surface 901 of the packing 900 to push the first pressing surface 406 of the outer tube 400; and
e) continuingly twisting the twisting portion 602 of the handle 600 and pushing the apparatus 10 by the outer tube 400, deforming the adjustable part 202 by the torque from the twisting portion 602 and making a press fit between the hole of the securing part 2011 and the tapered, tube end 121.

Figure 11:
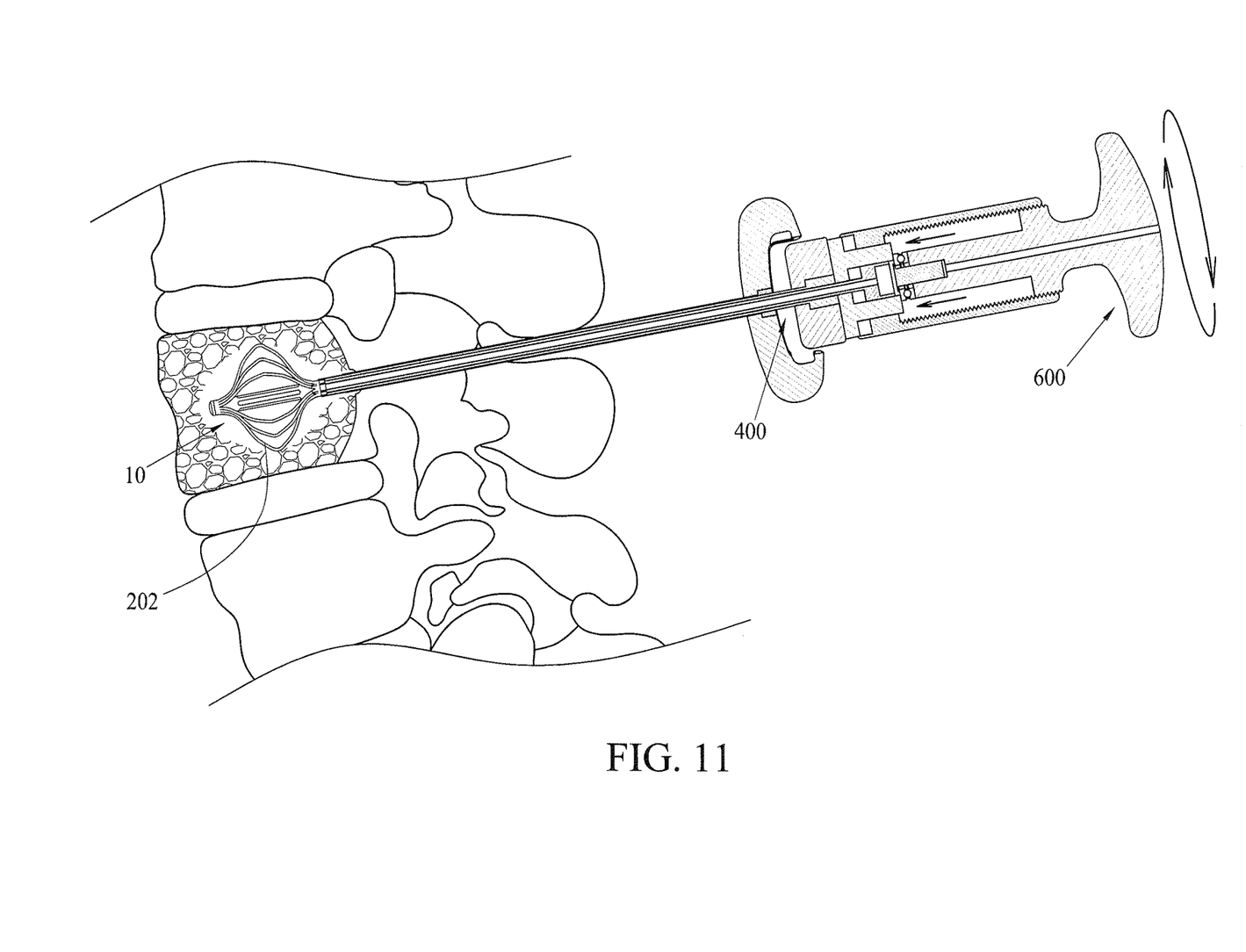
FIG. 11 is a schematic diagram showing the use state of an example of the present invention (implant expanded)

In the above description, the adjustable part 202 can form a curve with different gradients in the axial direction after expansion.

Figure 8:
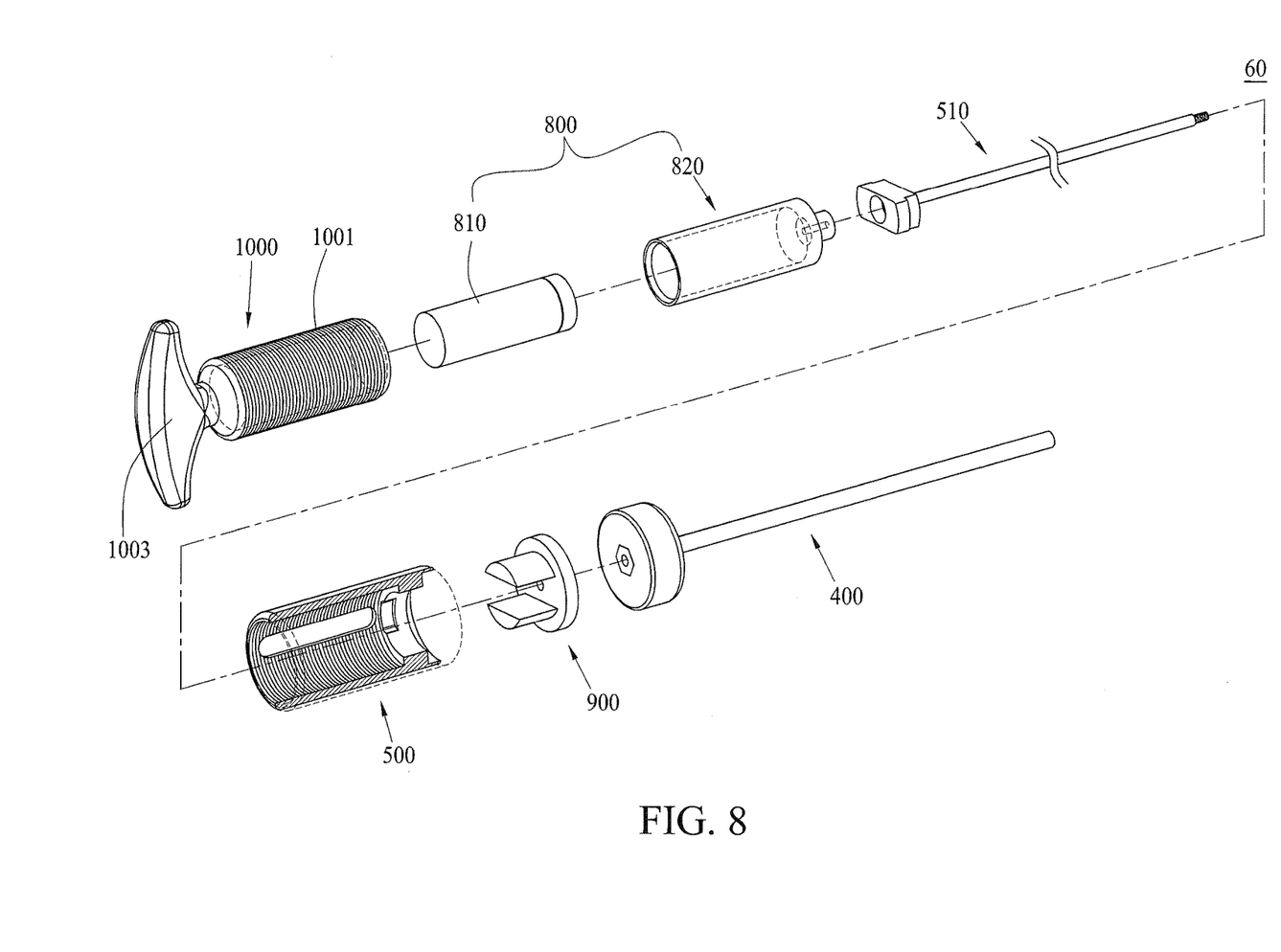
FIG. 8 shows a three-dimensional perspective view of an injector apparatus according to an illustrative embodiment of the present invention.
Figure 9:
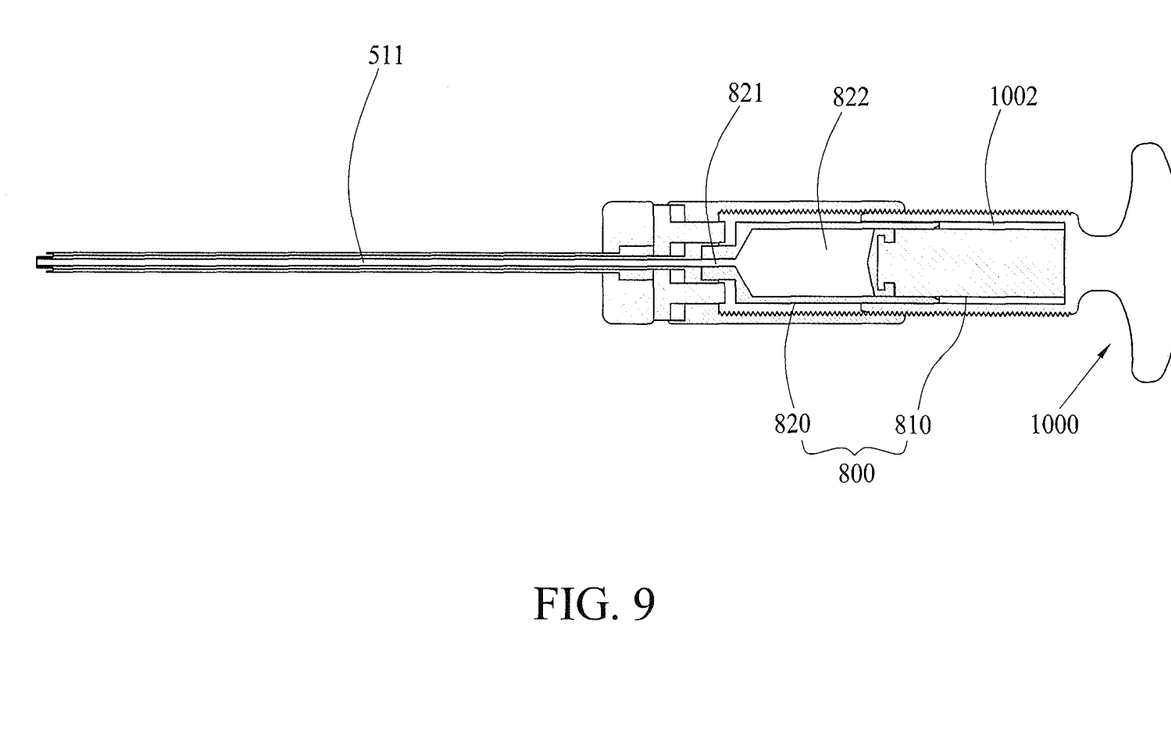
FIG. 9 shows a section view of the injector apparatus of the present invention.

In the above description, the handle 600 of the expanding apparatus 30 can be replaced by a container 800 for bone cement and an injecting handle 1000 to form an injector apparatus 60. The container 800 includes a piston 810 and a shell 820, and the piston 810 is movable in the axial direction and set within the shell 820. An exit 821 is formed at one side of the shell 820, and a room 822 is set within the shell 820 and connected to the exit 821. The room 822 is useful for accommodating a material 830, which is a mixture for reinforcing bone (e.g., bone cement). A second external thread 1001 is formed outside the injecting handle 1000, a chamber 1002 is set within one side of the injecting handle 1000, and a twisting part 1003 is formed at the other side in a wing shape for twisting. The second external thread 1001 is linked to the second inner thread 503. The container 800 is set at the chamber 1002 when the piston 810 is against the bottom of the chamber 1002, and the exit 821 is connected to the tunnel 511.

Figure 12:
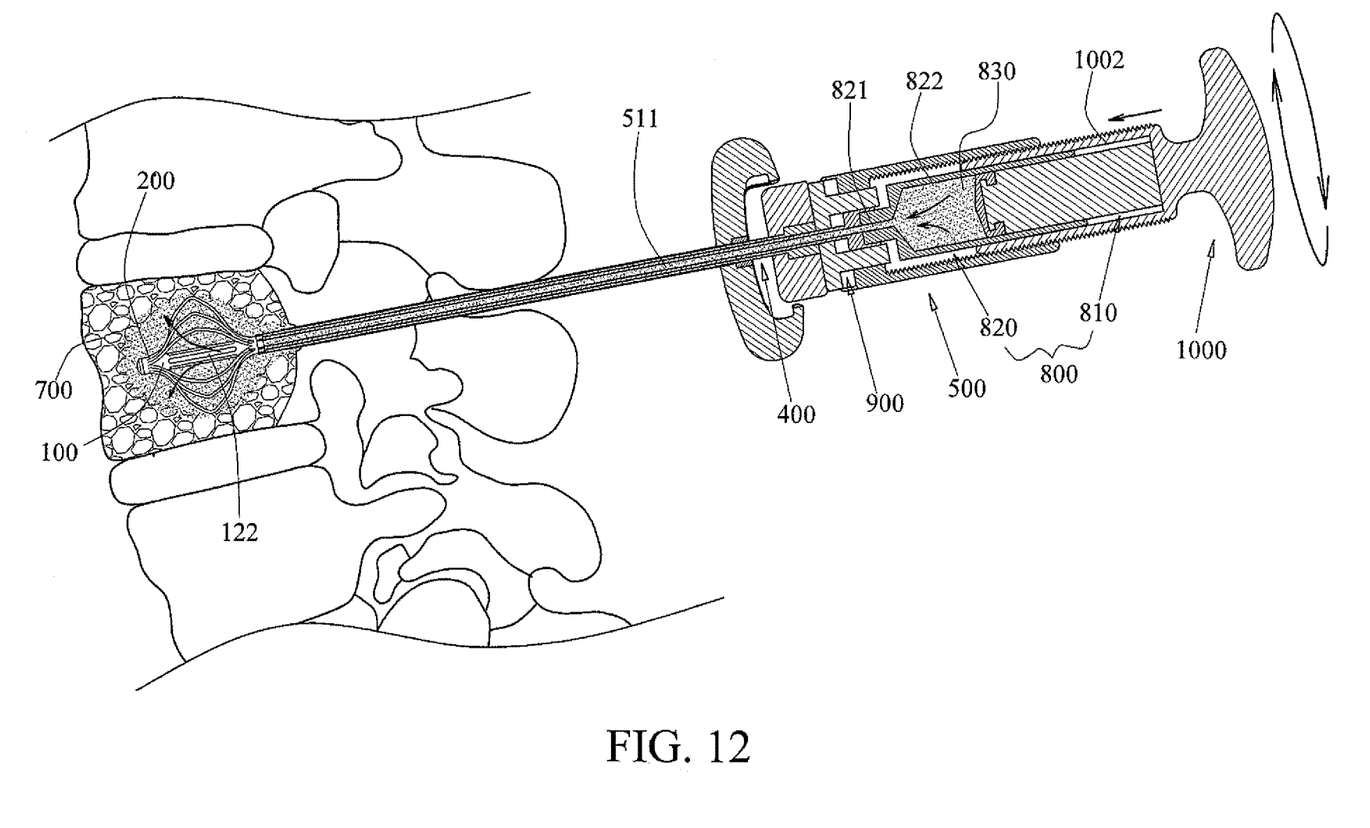
FIG. 12 is a schematic diagram showing the use state of an example of the present invention (injection with bone cement)
Figure 13:
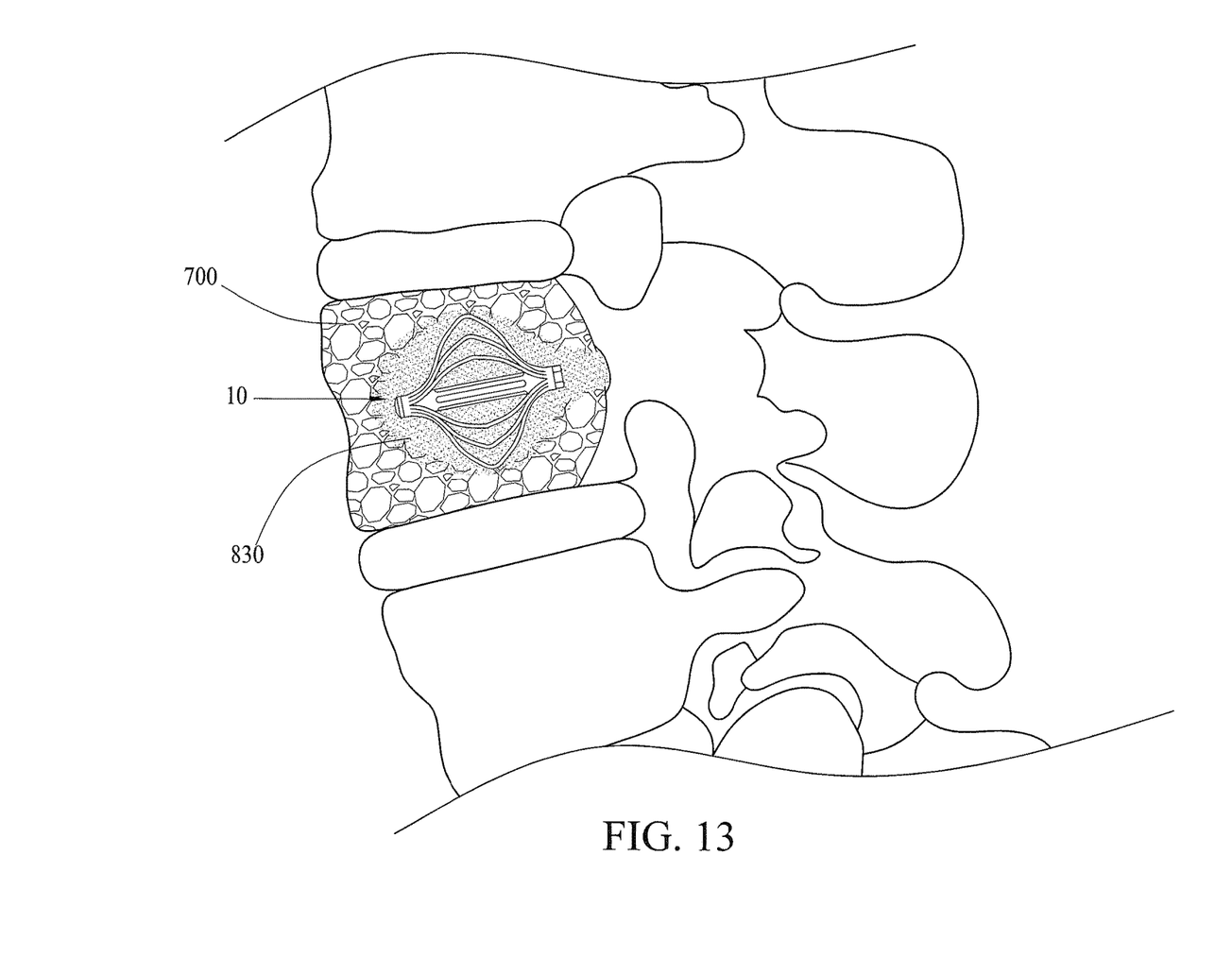
FIG. 13 is a schematic diagram of an example of the present invention showing the binding of an implant with bone cement in a vertebra.

The method to inject the material by using the aforesaid injector apparatus can be done by the following steps:

a) holding the hollow body 500 and twisting the twisting part 1003 or the injecting handle 1000, making the bottom of the chamber 1002 to push the piston 810 and enable the material 830 in the room 822 sequentially delivered out the exit 821, the tunnel 511, the device 100, the aperture 122, the barrel 200 and the window of the barrel, and into the damaged bone 700 to-be-treated; and b) relieving the injecting handle 1000, holding the base 405 of the outer tube 400, simultaneously twisting in a reverse direction of the hollow body 500, and ejecting the injection module.

While the invention has been described above with references to specific embodiments thereof, it can be seen that many changes, modifications and variations in the materials, arrangements of parts and steps can be made without departing from the inventive concept disclosed herein. Accordingly, the spirit and broad scope of the appended claims are intended to embrace all such changes, modifications and variations that may occur to one having skill in the art upon a reading of the disclosure.

The invention claimed is:

1. A kit including an apparatus for reinforcing a damaged bone and a tool for mounting the apparatus, with said apparatus comprising:
a cap;
a substantially rigid tube adjacent to the cap, wherein the substantially rigid tube comprises:
a tapered end which is distal to the cap;
an aperture which is proximal to the cap;
a threaded inner wall which allows the apparatus to be securely handled, wherein the inner threaded wall is proximal to the tapered end; and
a barrel encasing the substantially rigid tube, wherein the barrel comprises a securing part movable toward the cap in response to an external force and to be fixed at a desired position proximal to the tapered end of the substantially rigid tube, with the tool comprising an expanding apparatus comprising:
an outer tube having a through hole axially set within the outer tube, wherein a connection portion is set at one end of the outer tube, wherein the securing part is fitted in the connection portion, and a base is set at another end of the outer tube;
a separate inner coupling member, wherein a recess and a first fitting hole in an axial direction are set on the separate inner coupling member;
a hollow body, wherein the hollow body is void in a middle thereof, wherein an inner tube is formed within the hollow body, wherein a tunnel is axially set within the inner tube, wherein a lock is set at one side of the inner tube, wherein a first external threaded portion is set at another side of the inner tube, and wherein the first external threaded portion is connected to the threaded inner wall of the expanding apparatus to embed the lock into the recess, to restrict shift of the separate inner coupling member only in the axial direction on the hollow body; and
a handle, wherein a steering portion is connected to one side of the handle, and a twisting portion is set at another side of the handle;
wherein continuously exerting a twisting force to the handle makes the outer tube compress the expanding apparatus, and wherein an adjustable part of the expanding apparatus is compressed and deformed by twisting torque, to form an expandable implant of which an expanding degree and shape are adjustable.

2. The kit of claim 1, wherein a first pressing surface is set at one side of the base, wherein a second pressing surface is formed at one side of the separate inner coupling member and against the first pressing surface, wherein both sides of the recess form a third pressing surface, and wherein one side of the steering portion forms a fourth pressing surface.

3. The kit of claim 1, wherein a second fitting hole and a third fitting hole are sequentially set at one end within the hollow body, and wherein a second inner thread is set at another end of the hollow body; wherein the inner tube is sequentially fitted into the first fitting hole and the through hole; wherein a second external thread is formed outside the handle, and wherein the second external thread is linked to the second inner thread.

4. The kit of claim 3, wherein an outer rim and a fitting portion are set on the separate inner coupling member, wherein the fitting portion is fitted into the third fitting hole, and wherein the outer rim is fitted into the second fitting hole, to stop movement of the separate inner coupling member at the outer rim.

5. The kit of claim 3, further comprising an injector apparatus comprising:
a container and an injecting handle replacing the handle of the expanding apparatus after removal of the handle, wherein the container includes a piston and a shell, wherein the piston is movable in the axial direction and set within the shell; wherein an exit is formed at one side of the shell, and wherein a room is set within the shell and is connected to the exit; and wherein the room is for accommodating a material; and
an alternate second external thread formed outside the injecting handle, wherein a chamber is set within one side of the injecting handle, wherein a twisting part is formed at another side, wherein the alternate second external thread is linked to the second inner thread, and wherein the container is set at the chamber to move the piston in the chamber, and to allow the exit to connect to the tunnel;
wherein twisting the injecting handle moves an end surface of the chamber to push the piston to allow the material in the room to deliver out along the exit, the tunnel, the aperture, the barrel, and a window of the barrel, and into a treatment area.

6. The kit of claim 5, wherein the material is bone cement, and wherein the container is a container for bone cement.

7. The kit of claim 5, wherein the material is a mixture for reinforcing bone.

8. The kit of claim 1, wherein the adjustable part forms a curve with different gradients in the axial direction after expansion.

9. The kit of claim 1, wherein the steering portion is a bearing.

10. The kit of claim 1, wherein the steering portion transfers a direction of twisting force to an axis of the apparatus.

\* \* \* \* \*